(12) United States Patent
Andrews

(10) Patent No.: US 9,603,719 B2
(45) Date of Patent: Mar. 28, 2017

(54) SURGICAL EXTRACTION DEVICE

(71) Applicant: Scott Andrews, Flossmoor, IL (US)

(72) Inventor: Scott Andrews, Flossmoor, IL (US)

( * ) Notice: Subject to any disclaimer, the term of this patent is extended or adjusted under 35 U.S.C. 154(b) by 248 days.

(21) Appl. No.: 14/195,507

(22) Filed: Mar. 3, 2014

(65) Prior Publication Data

US 2015/0245920 A1   Sep. 3, 2015

(51) Int. Cl.
| | | |
|---|---|---|
| *A61F 2/46* | (2006.01) |
| *A61B 17/88* | (2006.01) |
| *B27B 27/02* | (2006.01) |
| *B25B 7/14* | (2006.01) |
| *B25B 7/12* | (2006.01) |
| *B25B 7/22* | (2006.01) |
| *A61B 17/92* | (2006.01) |
| *A61B 17/28* | (2006.01) |

(52) U.S. Cl.
CPC ............ *A61F 2/4603* (2013.01); *A61B 17/88* (2013.01); *A61B 17/8872* (2013.01); *A61B 17/92* (2013.01); *A61B 17/921* (2013.01); *A61F 2/461* (2013.01); *A61F 2/4684* (2013.01); *B25B 7/12* (2013.01); *B25B 7/14* (2013.01); *B25B 7/22* (2013.01); *B27B 27/02* (2013.01); *A61B 17/2804* (2013.01); *A61F 2002/4619* (2013.01); *A61F 2002/4628* (2013.01); *A61F 2002/4681* (2013.01)

(58) Field of Classification Search
CPC . A61B 17/2804; A61B 17/88; A61B 17/8872; A61B 17/92; A61F 2/4603; A61F 2/461; A61F 2002/4619; A61F 2002/4628; A61F 2002/4681; A61F 2/4684; B25B 7/12; B25B 7/14; B25B 7/22; B27B 27/02
See application file for complete search history.

(56) References Cited

U.S. PATENT DOCUMENTS

| | | | | |
|---|---|---|---|---|
| 1,832,879 | A | * | 11/1931 | Ruskin ............... A61B 17/2804 30/193 |
| 3,859,874 | A | * | 1/1975 | Joeckel ................... B25B 7/123 81/367 |
| 5,122,130 | A | | 6/1992 | Keller |
| 5,368,596 | A | | 11/1994 | Burkhart |

(Continued)

FOREIGN PATENT DOCUMENTS

| | | |
|---|---|---|
| DE | 2521127 | 11/1976 |
| WO | 2010136631 | 12/2010 |

OTHER PUBLICATIONS

Innomed brochure for Ortho Rongeur instrument, publicly available before Mar. 3, 2014.

(Continued)

*Primary Examiner* — Larry E Waggle, Jr.
(74) *Attorney, Agent, or Firm* — Michael Best & Friedrich LLP

(57) ABSTRACT

A surgical extraction device for extracting an orthopedic part or other hardware. The device includes a gripping portion at a distal end of the device and a handle portion and a strike plate at a proximal end of the device. The handle portion includes a body that includes a first handle and a second handle that are pivotably coupled to one another. The gripping portion includes a first gripping member and a second gripping member that are pivotably coupled to one another.

8 Claims, 5 Drawing Sheets

(56) References Cited

U.S. PATENT DOCUMENTS

| | | | | |
|---|---|---|---|---|
| 5,562,447 | A * | 10/1996 | Moy | A61C 8/0089 |
| | | | | 433/150 |
| 6,136,004 | A | 10/2000 | Keller | |
| 7,625,376 | B2 * | 12/2009 | Brumfield | B25B 7/18 |
| | | | | 606/86 A |
| 8,307,745 | B2 * | 11/2012 | Christensen, III | B25B 7/12 |
| | | | | 606/105 |
| 8,393,254 | B2 * | 3/2013 | Gao | A61B 17/2804 |
| | | | | 294/2 |
| 9,314,345 | B2 * | 4/2016 | Traynelis | A61F 2/44 |
| 2007/0156171 | A1 * | 7/2007 | Lang | A61F 2/461 |
| | | | | 606/205 |
| 2012/0143204 | A1 | 6/2012 | Blaylock et al. | |

OTHER PUBLICATIONS

European Search Report for EP Application No. 15157353.2 dated Jul. 1, 2015.

* cited by examiner

SURGICAL EXTRACTION DEVICE

BACKGROUND OF THE INVENTION

Joint replacement surgeries have become routine procedures for alleviating symptoms associated with dysfunctional joint surfaces. For example, joints can be damaged by arthritis and other diseases, injuries, and the like. Arthritis and years of use may cause the joint to wear away, which causes pain, stiffness, and swelling. Joint replacement surgeries typically include replacing all or part of the joint with a prosthesis that comprises mechanical parts designed to mimic the function of a natural joint. During the procedure of knee replacement, trials are placed in the knee that are similar to the final implants. These trials may be inserted and removed one or more times during the procedure. The process of removing the trials may be difficult. In addition, one or more of the final implants may be fixated to the bone by cement or by bony ingrowth. In the event that the prosthesis (implant) needs to be removed, the removal of one or more of the mechanical parts or prosthesis (implant) may require significant force.

SUMMARY OF THE INVENTION

The present invention relates to a surgical extraction device.

In one embodiment, the invention is a surgical extraction device comprising a first handle and a second handle pivotably coupled to the first handle. The device also includes a first gripping member pivotably coupled to the first handle, a second gripping member pivotably coupled to the second handle, the second gripping member pivotably coupled to the first gripping member, and a strike plate coupled to the first handle.

In another embodiment the invention is a surgical extraction device comprising a first handle and a second handle pivotably coupled to the first handle. The device also includes a first gripping member pivotably coupled to the first handle, the first gripping member including a proximal end and a distal end, and wherein a channel is formed at the distal end of the first gripping member and a second gripping member pivotably coupled to the second handle, the second gripping member pivotably coupled to the first gripping member.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
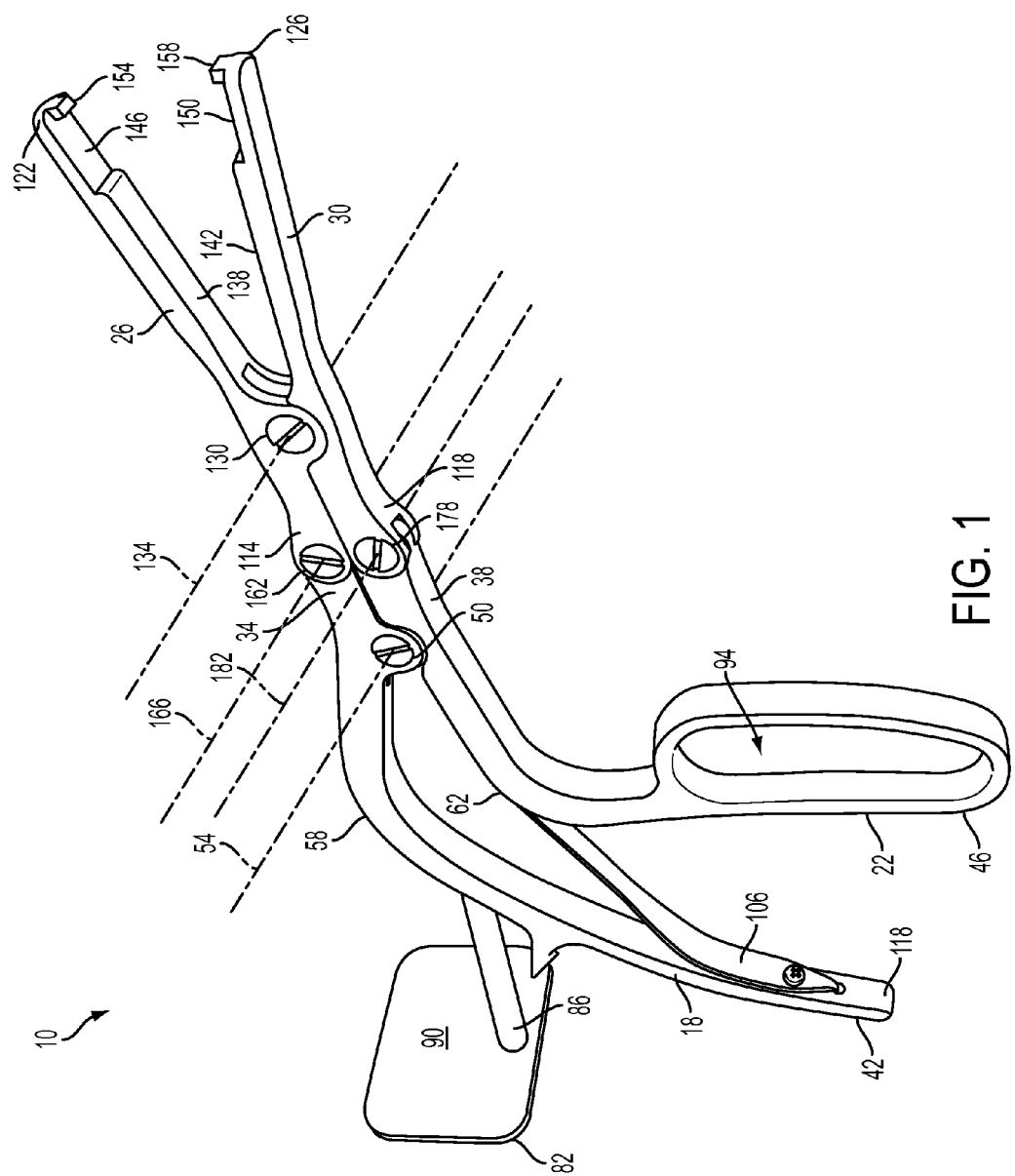
FIG. 1 is a front perspective view of a surgical extraction device according to one embodiment of the invention.

FIGS. 1-4 illustrate a surgical extraction device 10 according to one embodiment of the invention. As illustrated in FIG. 1, the surgical extraction device 10 includes a gripping portion at a distal end of the device 10 and a handle portion at a proximal end of the device 10. The handle portion includes a first handle 18 and a second handle 22. The gripping portion includes a first gripping member 26 and a second gripping member 30. A length of the device 10 defines a longitudinal axis A (see FIG. 2).

Each of the first handle 18 and the second handle 22 includes a first end 34, 38 and a second end 42, 46. The first handle 18 and the second handle 22 are pivotably coupled to one another by a fastener (i.e., a screw or the like) 50, which is positioned between the first ends 34, 38 and the second ends 42, 46 of each handle 18, 22. The first handle 18 and the second handle 22 are pivotable relative to one another about a first axis 54 (see FIG. 3) defined by the fastener 50. A portion 58, 62 of each of the first handle 18 and the second handle 22 is arcuately shaped such that, together, the first handle 18 and the second handle 22 define a pistol grip of the device 10.

Figure 2:
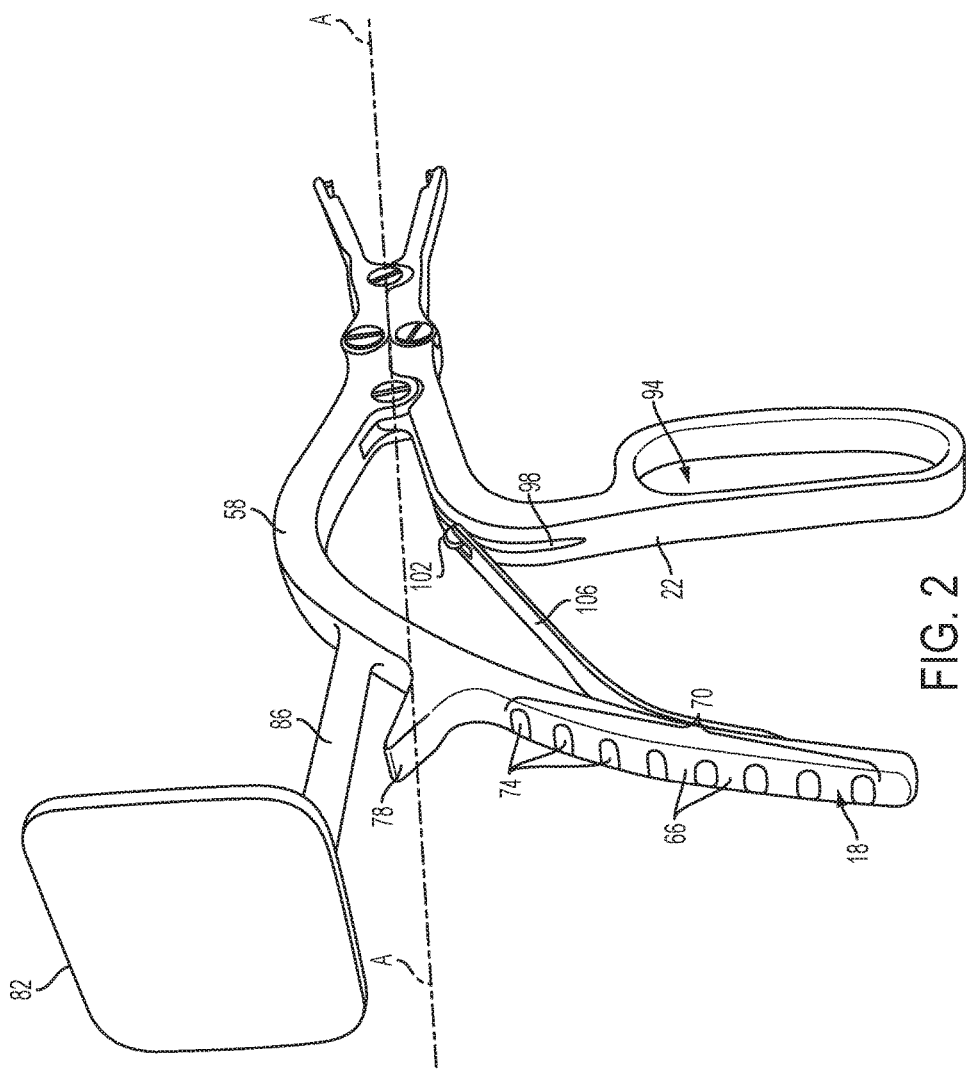
FIG. 2 is a rear perspective view of the surgical extraction device of FIG. 1.

With reference to FIG. 2, the first handle 18 includes a first surface 66 that has a contoured portion 70 covering at least a portion of the first surface 66. In the illustrated embodiment, the contoured portion 70 includes a plurality of grooves or indentations 74. The contoured portion 70 provides an anti-slip surface that helps the surgeon grip the first handle 18. The first handle 18 also includes an extension 78, which aids in stabilizing the hand of the surgeon on the device during use.

Figure 3:
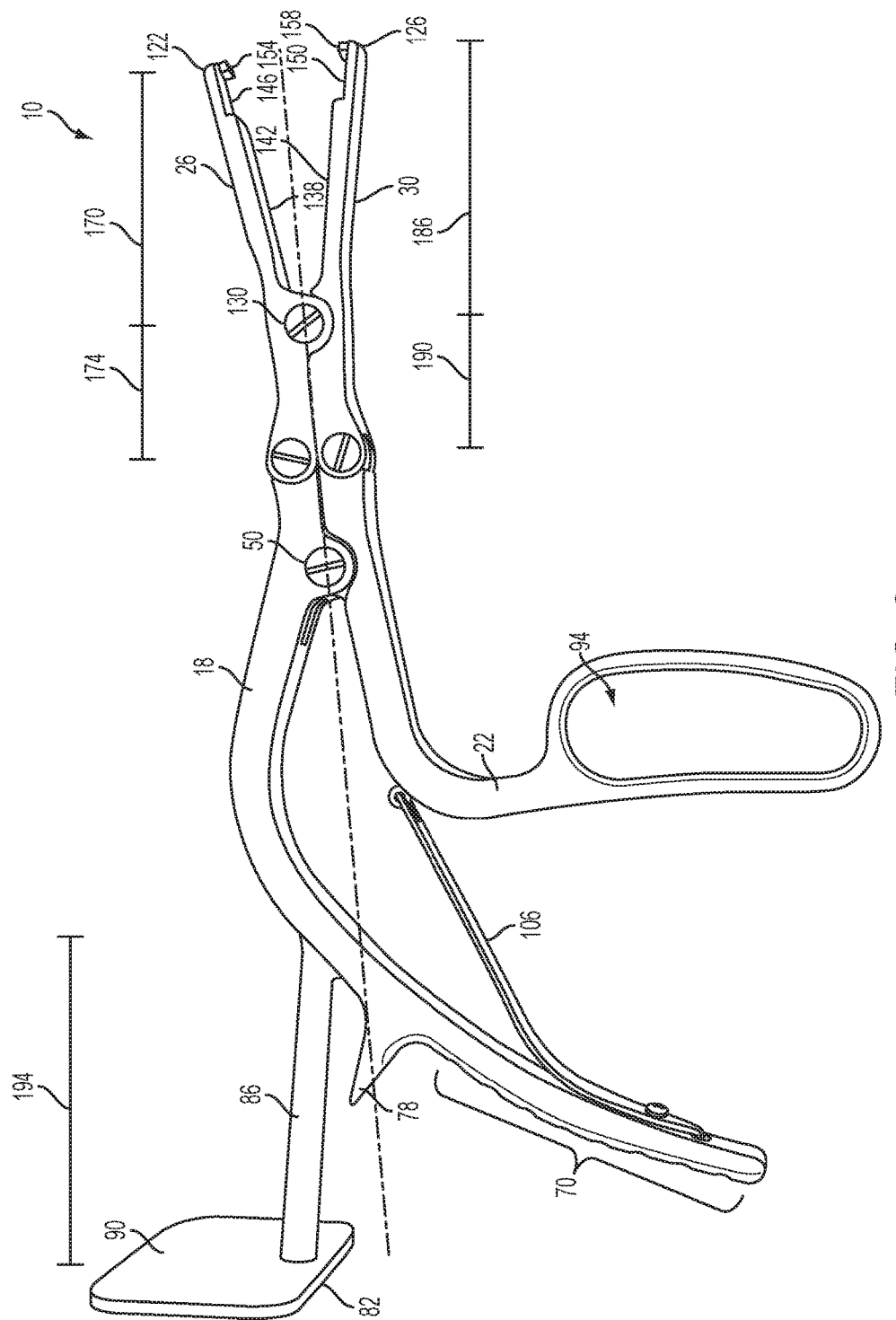
FIG. 3 is a side perspective view of the surgical extraction device of FIG. 1 in a first position.

As illustrated in FIGS. 1-3, the first handle 18 includes an strike plate 82 coupled thereto by a rod 86. In the illustrated embodiment, the strike plate 82 includes a force surface 90 that is a substantially square-shaped surface. In additional or alternative embodiments, the strike plate 82 may be any other suitable shape (i.e., circular, rectangular, etc.). Additionally, while in the illustrated embodiment, the first handle 18, the strike plate 82, and the rod 86 are integrally formed, other methods of joining (i.e., welding) may be employed to couple the first handle 18, the strike plate 82, and the rod 86 to one another.

The second handle 22 includes an aperture or opening 94 for receiving the fingers of the surgeon, however, the second handle 22 may be open (i.e., no aperture). In the open configuration of the second handle, the second handle 22 can includes indentations, ribs, prominences, etc. to allow for an anti-slip grip. The second handle 22 also includes a recess or channel 98 in which a pin 102 is slidably received. A link 106 is coupled to the pin 102 at one end and to a second surface 118 of the first handle 18 at a second end. When the first handle 18 and the second handle 22 are pivoted relative to one another about the fastener 50, the pin 102 slides within the channel 98.

With references to FIGS. 1 and 3, each of the first gripping member 26 and the second gripping member 30 include a first end 114, 118 and a second end 122, 126, respectively. The first gripping member 26 and the second gripping member 30 are pivotably coupled to one another by a fastener (i.e., a screw or the like) 130, which is positioned between the first end 114, 118 and the second end 122, 126 of each gripping member 26, 30. The first gripping member 26 and the second gripping member 30 are pivotable relative to one another about a second axis 134 that is defined by the fastener 130. The first axis 54 and the second axis 134 are spaced apart from one another along the longitudinal axis A but are oriented parallel to one another. Each of the first gripping member 26 and the second gripping member 30 includes a gripping or clamping surface 138, 142. A first channel 146 is formed in the gripping surface 138, and a second channel 150 is formed in the gripping surface 142. The channels 146, 150 are partially defined by a wall at the distal ends (i.e., at the second ends 122, 126) of the gripping member 26, 30 thereby defining a tooth or projection 154, 158.

Figure 4:
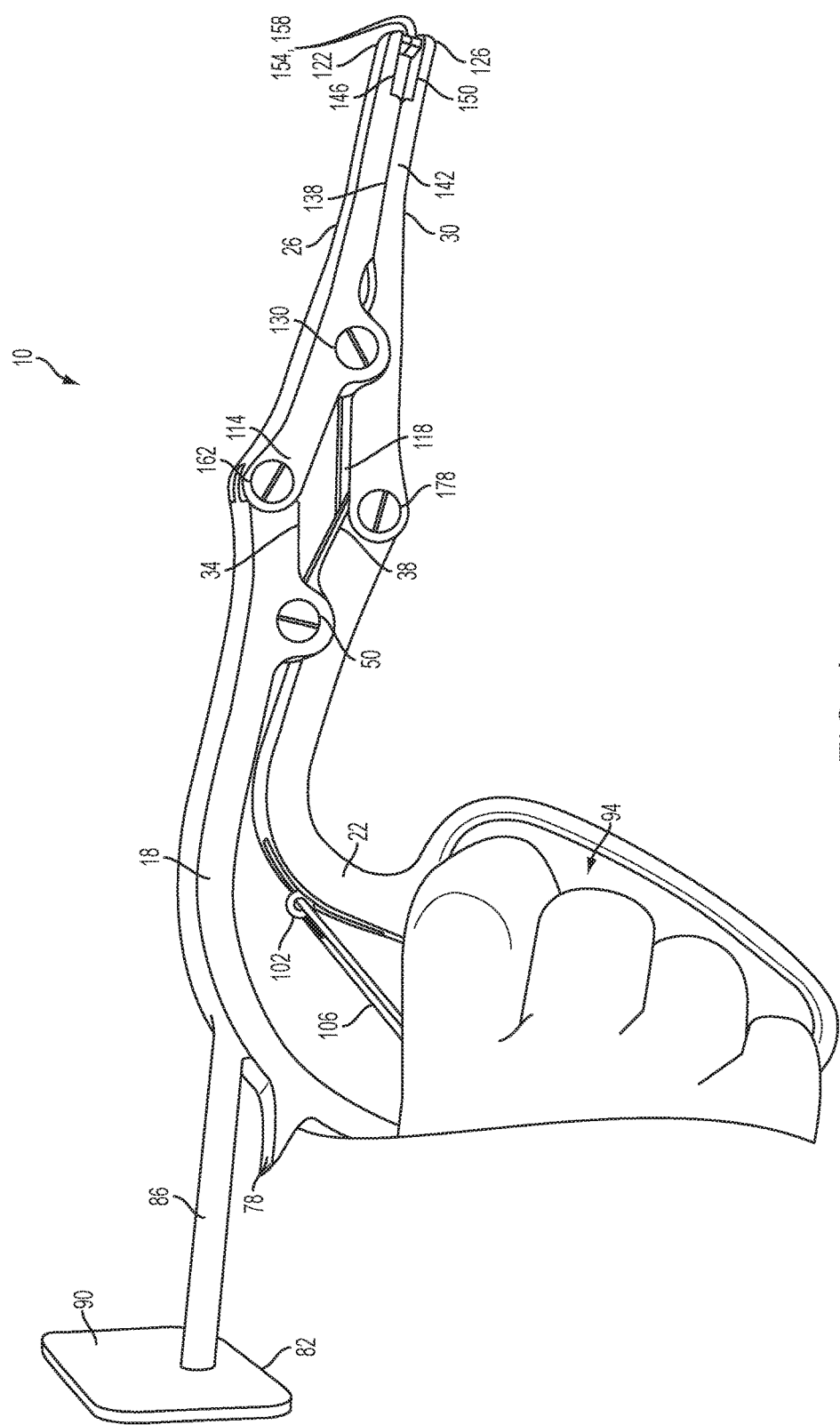
FIG. 4 is a side perspective view of the surgical extraction device of FIG. 1 in a second position.

With reference to FIGS. 1, 3, and 4, the first handle 18 is pivotably coupled to the first gripping member 26 by a fastener 162 such that the first gripping member 26 is pivotable relative to the first handle 18 about a third axis 166 (see FIG. 3). The fastener 162, and therefore the third axis 166, is positioned near the first end 114 of the first gripping member 26 and near the first end 34 of the first handle 18. Further, the second axis 134 is positioned between the first end 114 and the second end 122 of the first gripping member 26. A distance 170 between the second end 122 of the first gripping member 26 and the second axis 134 is greater than a distance 174 between the third axis 166 and the second axis 134. In one construction, and as illustrated in the figures, the distance 170 is greater than the distance 174 thereby creating an elongated gripping member. The elongated configuration is to accommodate the size of trials or hardware the tool is being used to remove. Further, the gripping members have to open wide enough to accommodate the width of the trials or hardware being extracted and then allow for adequate clamping force for their removal. In other constructions, the distances 170 and 174 may be the same or substantially the same.

Similarly, the second handle 22 is pivotably coupled to the second gripping member 30 by a fastener 178 such that the second gripping member 30 is pivotable relative to the second handle 22 about a fourth axis 182. The fourth axis 182 is substantially aligned with and spaced along the longitudinal axis A apart from the third axis 166. The fastener 178, and therefore the fourth axis 182, is positioned near the first end 118 of the second gripping member 30 and near the first end 38 of the second handle 22. Further, the second axis 134 is positioned between the first end 118 and the second end 126 of the second gripping member 30. A distance 186 between the second end 126 of the second gripping member 30 and the second axis 134 is greater than a distance 190 between the fourth axis 182 and the second axis 134. In one construction, and as illustrated in the figures, the distance 186 is greater than the distance 190 thereby creating an elongated gripping member. The elongated configuration is to accommodate the size of trials the tool or hardware is being used to remove. Further, the gripping members have to open wide enough to accommodate the width of the trials or hardware being extracted and then allow for adequate clamping force for their removal. In other constructions, the distances 186 and 190 may be the same or substantially the same.

The gripping surfaces 138, 142 extend between the second axis 134 (i.e., where the gripping members 26, 30 are coupled) to the second ends 122, 126 of the first and the second gripping members 26, 30. Therefore, the gripping surfaces 138, 142 are elongated. As illustrated, the first axis 54, second axis 134, third axis 166, and fourth axis 182 are oriented in parallel to one another. Further, the third axis 166 and the fourth axis 182 are positioned between the first axis 54 and the second axis 134 such that pivoting motion of the handles 18, 22 relative to one another causes the gripping members 26, 30 to pivot about the fasteners 162, 178, and therefore, the third and fourth axes 166, 182, as shown in FIG. 4.

As illustrated in FIGS. 1-4, the first handle 18 and the second handle 22 are configured to pivot the first gripping member 26 and the second gripping member 30 relative to one another for gripping trials or other hardware therebetween. Moving or pivoting the first handle 18 and the second handle 22 relative to one another between a first position (FIG. 3) and second position (FIG. 4) causes the first gripping member 26 and the second gripping member 30 to pivot relative to one another between an unclamped position (FIG. 3) and a clamped position (FIG. 4).

In particular, when the first handle 18 is moved closer to the second handle 22, the first gripping member 26 and the second gripping member 30 move from the unclamped position to the clamped position. In doing so, the first end 114 of the first gripping member 26 and the first end 118 of the second gripping member 30 move away from one another and the second end 122 of the first gripping member 26 and the second end 126 of the second gripping member 114 move toward one another. In other words, the gripping surfaces 138, 142 of the first gripping member 26 and the second gripping member 30, respectively, move toward one another from the unclamped position to the clamped position. When the device 10 is in the clamped position, the channels 146, 150 and the teeth 154, 158 cooperate in securing the trials or other hardware that is to be extracted or removed between the first and the second gripping members 26, 30.

Additionally, the length of the gripping surfaces 138, 142 allows the surgeon to insert the device 10 deep within the body cavity to grasp orthopedic trials, prostheses, and hardware. Once the tissue or orthopedic part is secured between the first and the second gripping members 26, 30, the surgeon may exert a force away from the cavity to remove the orthopedic part. If the surgeon requires additional force to remove the orthopedic part, the surgeon may apply extra force (i.e., with a surgical mallet or the like) to the force surface 90 of the strike plate 82 in order to remove the orthopedic part. Therefore, the strike plate 82 may be spaced apart from the first handle 18 by any suitable distance (i.e., a length 194 of the rod 86) that accommodates another surgical tool to provide a striking force against the force surface 90.

Similarly, when the first handle 18 is pivoted away from the second handle 22, the first gripping member 26 and the second gripping member 30 move from the clamped position to the unclamped position. In doing so, the first end 114 of the first gripping member 26 and the first end 118 of the second gripping member 30 move toward one another and the second end 122 of the first gripping member 26 and the second end 126 of the second gripping member 114 move away from one another from the clamped position to the unclamped position. In other words, the gripping surfaces 138, 142 of the first gripping member 26 and the second gripping member 30, respectively, move away from one another.

Figure 5:
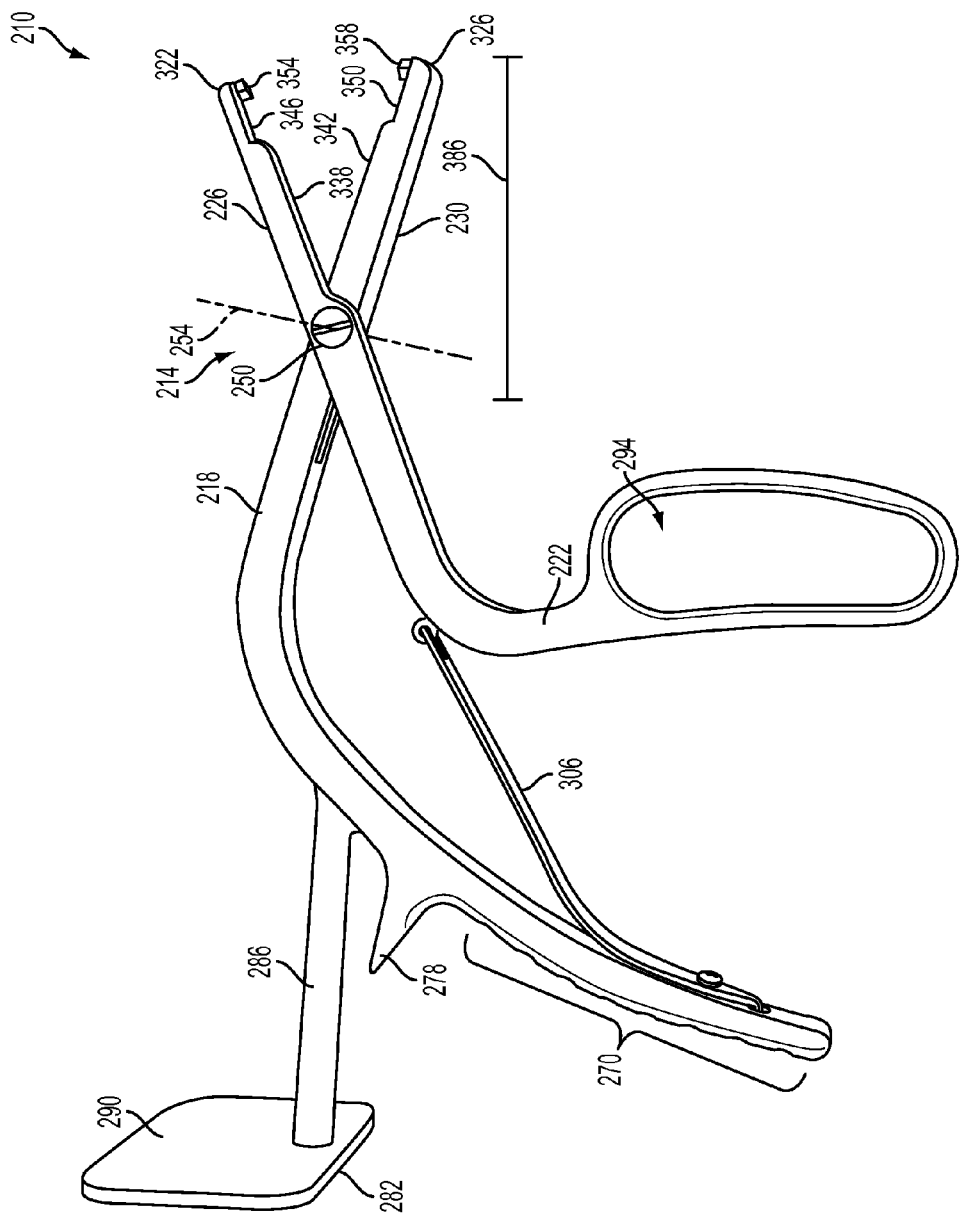
FIG. 5 is a side perspective view of a surgical extraction device according to another embodiment of the invention.

FIG. 5 illustrates a surgical extraction device 210 according to another embodiment of the invention. The surgical extraction device 210 of FIG. 5 is similar to the surgical extraction device of FIGS. 1-4; therefore, like structure will be identified by like reference numbers plus "200" and only the differences will be discussed hereafter.

The surgical extraction device 210 includes a first handle 218 and a second handle 222 that are pivotably coupled to one another by a fastener 250. A first gripping member 226 and a second gripping member 230 are pivotably coupled to one another by the fastener 250, as well. In the embodiment illustrated in FIG. 5, the first handle 218 is formed as one piece with the gripping member 230 and the second handle 222 is formed as one piece with the gripping member 226. In other additional or alternative embodiments, each of the first and the second handles 218, 222 and the first and the second gripping members 226, 230 may be unique components. In either case, the fastener 250 couples the first handle 218, the second handle 222, the first gripping member 226, and the second gripping member 230 together. The first handle 218 and the second handle 222 are pivotable relative to one another about an axis 254 that is defined by the fastener 250. Similarly, the first gripping member 226 and the second gripping member 230 are pivotable relative to one another about the axis 254 that is defined by the fastener 250. A distance 386 between the axis 254 second ends 322, 326 of the first and the second gripping members 226, 230 creates an elongated gripping member. The elongated configuration is to accommodate the size of trials or hardware the tool is being used to remove. Further, the gripping members have to open wide enough to accommodate the width of the trials or hardware being extracted and then allow for adequate clamping force for their removal.

Similar to the embodiment of FIGS. 1-4, the first handle 218 and the second handle 222 are configured to pivot the first gripping member 226 and the second gripping member 230 relative to one another for gripping trials or other hardware therebetween. Moving or pivoting the first handle 218 and the second handle 222 relative to one another between a first position and second position causes the first gripping member 226 and the second gripping member 230 to pivot relative to one another between an unclamped position and a clamped position about axis 254.

Thus, the invention provides, among other things, a surgical extraction device that includes a strike plate, a pistol type grip, and elongated gripping surfaces that have a channel and a tooth. Various features and advantages of the invention are set forth in the following claims.

What is claimed is:

1. A surgical extraction device comprising:
  a first curved handle;
  a second curved handle pivotably coupled to the first curved handle;
  a first gripping member pivotably coupled to the first curved handle;
  a second gripping member pivotably coupled to the second curved handle, the second gripping member pivotably coupled to the first gripping member;
  a rod extending from the first curved handle between a proximal end of the first curved handle and a proximal end of the first gripping member; and
  a strike plate coupled to the rod, the strike plate partially extending above an upper-most portion of the first curved handle,
  wherein the first handle is pivotable relative to the second handle about a first axis, and the first gripping member is pivotable relative to the second gripping member about a second axis, the first axis and the second axis being spaced apart from one another,
  wherein the first gripping member is pivotable relative to the first handle about a third axis, and the second gripping member is pivotable relative to the second handle about a fourth axis, the third axis and the fourth axis being spaced apart from one another,
  wherein the first gripping member includes a first end and a second end, the third axis being positioned near the first end and the second axis being positioned between the first end and the second end,
  wherein the second gripping member includes a first end and second end, the fourth axis being positioned near the first end and the second axis being positioned between the first end and the second end,
  wherein a distance between the second end of the first gripping member and the second axis is greater than a distance between the third axis and the second axis, and
  wherein a distance between the second end of the second gripping member and the second axis is greater than a distance between the fourth axis and the second axis.

2. The surgical extraction device of claim 1, wherein each of the first gripping member and the second gripping member includes a channel.

3. The surgical extraction device of claim 1, wherein each of the first gripping member and the second gripping member includes a tooth at a distal end.

4. The surgical extraction device of claim 1, wherein the third axis and the fourth axis are positioned between the first axis and the second axis.

5. The surgical extraction device of claim 1, wherein the first axis, second axis, third axis, and fourth axis are oriented parallel to one another.

6. The surgical extraction device of claim 1, wherein moving the first handle closer to the second handle moves the device from an unclamped position to a clamped position such that the first end of the first gripping member and the first end of the second gripping member move away from one another and the second end of the first gripping member and the second end of the second gripping member move toward one another.

7. The surgical extraction device of claim 1, wherein moving the first handle away from the second handle moves the device from a clamped position to an unclamped position such that the first end of the first gripping member and the first end of the second gripping member move toward one another and the second end of the first gripping member and the second end of the second gripping member move away from one another.

8. A surgical extraction device comprising:
  a first handle;
  a second handle pivotably coupled to the first handle;
  a first gripping member pivotably coupled to the first handle, the first gripping member including a proximal end and a distal end, and wherein a channel is formed at the distal end of the first gripping member;
  a second gripping member pivotably coupled to the second handle, the second gripping member pivotably coupled to the first gripping member;
  a rod extending from the first handle between a proximal end of the first handle and a proximal end of the first gripping member; and
  a strike plate extending perpendicular to the rod at an off-center location,
  wherein the first handle is pivotable relative to the second handle about a first axis, and the first gripping member is pivotable relative to the second gripping member about a second axis, the first axis and the second axis being spaced apart from one another,
  wherein a third axis extends perpendicular to the first axis and the second axis, and
  wherein the rod defines a fourth axis extending at an acute angle relative to the third axis.

* * * * *